United States Patent
Grass et al.

(10) Patent No.: US 10,258,303 B2
(45) Date of Patent: Apr. 16, 2019

(54) APPARATUS FOR DETERMINING A FRACTIONAL FLOW RESERVE VALUE

(71) Applicant: KONINKLIJKE PHILIPS N.V., Eindhoven (NL)

(72) Inventors: Michael Grass, Buchholz in der Nordheide (DE); Yechiel Lamash, Haifa (IL); Liran Goshen, Pardes-Hanna (IL); Holger Schmitt, Luetjensee (DE); Mordechay Pinchas Freiman, Pardes-Hanna (IL); Hannes Nickisch, Hamburg (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 135 days.

(21) Appl. No.: 15/317,158

(22) PCT Filed: Jun. 24, 2015

(86) PCT No.: PCT/EP2015/064168
§ 371 (c)(1),
(2) Date: Dec. 8, 2016

(87) PCT Pub. No.: WO2016/001017
PCT Pub. Date: Jan. 7, 2016

(65) Prior Publication Data
US 2017/0105694 A1 Apr. 20, 2017

(30) Foreign Application Priority Data
Jun. 30, 2014 (EP) .................................... 14174891

(51) Int. Cl.
*A61B 5/04* (2006.01)
*A61B 6/00* (2006.01)
(Continued)

(52) U.S. Cl.
CPC .......... *A61B 6/507* (2013.01); *A61B 5/02007* (2013.01); *A61B 5/029* (2013.01);
(Continued)

(58) Field of Classification Search
USPC .................................................. 600/431, 438
See application file for complete search history.

(56) References Cited

U.S. PATENT DOCUMENTS

| 8,157,742 B2 | 4/2012 | Taylor |
| 8,200,466 B2 | 6/2012 | Spilker |

(Continued)

FOREIGN PATENT DOCUMENTS

| DE | 102008014792 | 6/2009 |
| JP | 2011245159 | 12/2011 |

(Continued)

OTHER PUBLICATIONS

Prevrhal, et al., "CT Angiograhic Measurement of Vascular Blood Flow Velocity by Using Projection Data", Radiology, vol. 261, No. 3, pp. 923 to 929 (2011).

(Continued)

*Primary Examiner* — Nicole F Lavert (57) ABSTRACT

The invention relates to an apparatus for determining a fractional flow reserve (FFR) value of the coronary artery system of a living being (3). A fractional flow reserve value determination unit (13) determines the FFR value by using an FFR value determination algorithm that is adapted to determine the FFR value based on a boundary condition and a provided representation of the coronary artery system, wherein the boundary condition is specific for the living being and determined by a boundary condition determination unit (12). Since the boundary condition determination unit determines a boundary condition, which is specific for the living being, and since the fractional flow reserve value (Continued)

determination unit not only uses the provided representation of the coronary artery system, but also the living being specific boundary condition for determining the FFR value, the accuracy of the FFR value, which is non-invasively determined, can be improved.

20 Claims, 5 Drawing Sheets (51) Int. Cl.
    *G16H 50/50*     (2018.01)
    *A61B 5/02*     (2006.01)
    *A61B 6/03*     (2006.01)
    *A61B 6/06*     (2006.01)
    *A61B 5/029*     (2006.01)

(52) U.S. Cl.
    CPC ............ *A61B 6/032* (2013.01); *A61B 6/06* (2013.01); *A61B 6/4078* (2013.01); *A61B 6/4233* (2013.01); *A61B 6/481* (2013.01); *A61B 6/486* (2013.01); *A61B 6/503* (2013.01); *A61B 6/504* (2013.01); *A61B 6/5217* (2013.01); *A61B 6/5288* (2013.01); *A61B 6/54* (2013.01); *G16H 50/50* (2018.01); *A61B 6/482* (2013.01)

(56) References Cited

U.S. PATENT DOCUMENTS

| | | | |
|---|---|---|---|
| 8,249,815 B2 | 8/2012 | Taylor | |
| 2010/0130878 A1 | 5/2010 | Lasso | |
| 2010/0241404 A1 | 9/2010 | Taylor | |
| 2011/0274333 A1 | 11/2011 | Prevrhal | |
| 2011/0307231 A1 | 12/2011 | Kirchner | |
| 2012/0022843 A1 | 1/2012 | Ionasec | |
| 2012/0041318 A1 | 2/2012 | Taylor | |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor | |
| 2012/0041325 A1 | 2/2012 | Taylor | |
| 2012/0041739 A1 | 2/2012 | Taylor | |
| 2012/0053918 A1* | 3/2012 | Taylor | A61B 5/02 703/9 |
| 2012/0053919 A1 | 3/2012 | Taylor | |
| 2012/0059246 A1 | 3/2012 | Taylor | |
| 2012/0072190 A1 | 3/2012 | Sharma | |
| 2012/0121151 A1 | 5/2012 | Bernhardt | |
| 2012/0243761 A1 | 9/2012 | Senzig | |
| 2013/0132054 A1 | 5/2013 | Sharma | |
| 2013/0172734 A1 | 7/2013 | Hsieh | |
| 2013/0246034 A1 | 9/2013 | Sharma | |
| 2013/0261441 A1 | 10/2013 | Das | |
| 2013/0324842 A1 | 12/2013 | Mittal | |
| 2014/0003688 A1 | 1/2014 | Hansis | |
| 2014/0058715 A1 | 2/2014 | Sharma | |
| 2014/0073976 A1 | 3/2014 | Fonte | |

FOREIGN PATENT DOCUMENTS

| | | |
|---|---|---|
| WO | 2004025572 | 3/2004 |
| WO | 200661814 | 6/2006 |
| WO | 200661815 | 6/2006 |
| WO | 201022762 | 3/2010 |
| WO | 2013/171644 | 11/2013 |
| WO | 2014/072861 | 5/2014 |
| WO | 2014/091339 | 6/2014 |

OTHER PUBLICATIONS

Koo et al., "Diagnosis of ischemia-causing coronary stenoses by noninvasive fractional flow reserve computed from coronary computed tomographic angiograms. Results from the prospective multicenter DISCOVER-FLOW (Diagnosis of Ischemia-Causing Stenoses Obtained Via Noninvasive Fractional Flow Reserve) study", Journal of the American College of Cardiology, 58 (19), pp. 1989 to 1997 (2011).

Kim et al., "Patient-specific modeling of blood flow and pressure in human coronary arteries", Annals of Biomedical Engineering 38(10), pp. 3195 to 3209 (2010).

Vignon-Clementel et al., "Outflow boundary conditions for three-dimensional simulations of non-periodic blood flow and pressure fields in deformable arteries", 13(5), pp. 625 to 640 (2010).

Pijls NH, De Bruyne B, Peels K, et al. "Measurement of fractional flow reserve to assess the functional severity of coronary-artery stenoses". N. Engl. J. Med. 334 (26): 1703-8, Jun. 1996.

Pijls NH, Van Gelder B, Van der Voort P et al. "Fractional flow reserve. A useful index to evaluate the influence of an epicardial coronary stenosis on myocardial blood flow". Circulation. 1995; 92: 3183-3193.

Taylor CA, Figueroa CA. "Patient-Specific Modeling of Cardiovascular Mechanics". Annual Review of Biomedical Engineering, vol. 11: 109-134, Aug. 2009.

Wilson, R. F., et al. "Effects of adenosine on human coronary arterial circulation." Circulation 82.5 (1990): 1595-1606.

Chamuleau, Steven AJ, et al. "Association between coronary lesion severity and distal microvascular resistance in patients with coronary artery disease." American Journal of Physiology—Heart and Circulatory Physiology 285.5 (2003): H2194-H2200.

Verhoeff, B. J., Siebes, M., Meuwissen, M., Atasever, B., Voskuil, M., de Winter, R. J.,& Piek, J. J. (2005). "Influence of percutaneous coronary intervention on coronary microvascular resistance index". Circulation, 111(1), 76-82.

Sen, Sayan, et al. "Development and Validation of a New Adenosine-Independent Index of Stenosis Severity From Coronary Wave-Intensity AnalysisResults of the ADVISE (ADenosine Vasodilator Independent Stenosis Evaluation) Study." Journal of the American College of Cardiology 59.15 (2012): 1392-1402.

Huo Y, Kassab GS. "Intraspecific scaling laws of vascular trees". J. R. Soc. Interface published online Jun. 15, 2011.

Indermühle, Andreas, et al. "Myocardial blood volume and coronary resistance during and after coronary angioplasty." American Journal of Physiology—Heart and Circulatory Physiology 300.3 (2011): H1119-H1124.

\* cited by examiner

FIG. 8

APPARATUS FOR DETERMINING A FRACTIONAL FLOW RESERVE VALUE

CROSS REFERENCE TO RELATED APPLICATIONS

This application is the U.S. National Phase application under 35 U.S.C. § 371 of International Application No. PCT/EP2015/064168, filed Jun. 24, 2015, published as WO 2016/001017 on Jan. 7, 2016, which claims the benefit of European Patent Application Number 14174891.3 filed Jun. 30, 2014. These applications are hereby incorporated by reference herein.

FIELD OF THE INVENTION

The invention relates to an apparatus, a method and a computer program for determining a fractional flow reserve (FFR) value of the coronary artery system of a living being.

BACKGROUND OF THE INVENTION

Granted U.S. Pat. No. 8,157,742 discloses a system for planning a treatment of a patient. The system comprises a computer system configured to receive patient-specific data regarding a geometry of an anatomical structure of the patient, to create a three-dimensional model representing at least a portion of the anatomical structure of the patient based on the patient specific data, and to determine a first FFR value within the anatomical structure of the patient based on the three-dimensional model and a physics-based model relating to the anatomical structure of the patient. The computer system is further configured to modify the three-dimensional model and to determine a second FFR value within the anatomical structure of the patient based on the modified three-dimensional model.

Granted U.S. Pat. No. 9,119,540 discloses an apparatus for non-invasively assessing a coronary artery disease based on medical image data. The apparatus comprises a means for generating an anatomical model of a coronary artery from medical image data and a means for estimating a velocity of blood in the coronary artery based on a spatio-temporal representation of contrast agent propagation in the medical image data. The apparatus further comprises a means for simulating blood flow in the anatomical model of the coronary artery using a computational fluid dynamics simulation that uses the estimated velocity of the blood in the coronary artery as a boundary condition.

Granted U.S. Pat. No. 9,757,073 discloses a system being adapted to determine an FFR value for a cardiac vessel having a stenosis based on extracted features and based on a learning model, wherein the extracted features have been extracted from segmented image data showing the cardiac vessel and the stenosis.

The article "CT Angiograhic Measurement of Vascular Blood Flow Velocity by Using Projection Data" by S. Prevrhal et al., Radiology, volume 261, number 3, pages 923 to 929 (2011) discloses a method for measuring a blood flow velocity by using projection data from CT scans.

Granted U.S. Pat. No. 9,867,584 discloses a system for determining a blood flow through coronary arteries. The system is adapted to generate a three-dimensional image data set of the coronary arteries and the myocardial muscle, to generate a three-dimensional marker data set of the myocardial muscle from a dual-energy or spectral three-dimensional data set obtained after administration of a marker, wherein the three-dimensional marker data set indicates the amount of the marker contained within voxels of the myocardial muscle, and to subdivide the myocardial muscle into myocardial muscle segments. The system is further adapted to determine which coronary artery supplies the respective myocardial muscle segment, to determine the volume of blood that flows into the respective myocardial muscle segments from the three-dimensional marker data set, and to determine the total volume of blood that flows into a coronary artery of interest by summing the volume of blood flowing into all myocardial muscle segments supplied by the coronary artery.

The FFR value of the coronary system is an important predictor of vascular health and typically measured invasively in a catheterization laboratory during percutaneous coronary interventions (PCIs). Alternatively, the fluid dynamics within the coronary system can be simulated based on a computed tomography (CT) image of the coronary system, in order to determine the FFR value. Determining the FFR value based on the simulation has the advantage that it can be determined non-invasively. However, the accuracy of the FFR value may be reduced in comparison to the invasively determined FFR value.

SUMMARY OF THE INVENTION

It is an object of the present invention to provide an apparatus, a method and a computer program for determining an FFR value of the coronary artery system of the living being, which allows for a non-invasive determination of this value with improved accuracy.

In a first aspect of the present invention an apparatus for determining an FFR value of the coronary artery system of a living being is presented, wherein the apparatus comprises:
  a representation providing unit for providing a representation of the coronary artery system,
  a fractional flow reserve value determination unit for determining the FFR value by using an FFR value determination algorithm that is adapted to determine the FFR value based on a boundary condition and the provided representation of the coronary artery system,
  providing projection data having been generated by a detector over time based on radiation, which is generated by a radiation source and which has traversed the aorta of the living being, while a contrast agent has flown through the aorta, by a projection data providing unit, wherein the detector has several rows of detection elements used for generating the projection data and wherein the radiation source is adapted such that not all rows of detection elements are irradiated, but only one row is irradiated by a single fan beam or some rows are irradiated by several fan beams,
  a boundary condition determination unit for determining a boundary condition which is specific for the living being based on the provided projection data.

Since the boundary condition determination unit determines a boundary condition, which is specific for the living being, and since the fractional flow reserve value determination unit not only uses the provided representation of the coronary artery system, but also the living being specific boundary condition for determining the FFR value, the accuracy of the FFR value, which is non-invasively determined, can be improved.

The representation providing unit can comprise a storing unit for storing an already determined representation of the coronary artery system and for providing the stored representation. The representation providing unit can also comprise a receiving unit for receiving an already generated representation of the coronary artery system and for providing the received representation. Moreover, the representation providing unit can be adapted to generate the representation of the coronary artery system and to provide the generated representation. The representation is preferentially a three-dimensional representation of the coronary artery system. It is preferentially generated by segmenting the coronary artery system in a cardiac CT data set.

The boundary condition determination unit may be adapted to reconstruct a CT image and to determine a boundary condition based on a CT image and/or the boundary condition determination unit may be adapted to determine a boundary condition directly based on the provided projection data. Since the temporal resolution of the projection data can be much better than the temporal resolution of, for instance, reconstructed CT images, which may be reconstructed based on the projection data, by determining the boundary condition directly based on the projection data the accuracy of determining the FFR value can be further improved.

The projection data are generated by using one or several fan beams and the boundary condition determination unit is adapted to determine the boundary condition based on the projection data generated by the one or several fan beams. However, the projection data can also be generated by using a cone beam and the boundary condition determination unit can be adapted to determine the boundary condition based on the projection data generated by the cone beam.

In an embodiment, the detector has several rows of detection elements used for generating the projection data, wherein the radiation source is adapted such that not all rows of detection elements are irradiated by a cone beam, but only some rows by fan beams. A fan beam is preferentially regarded as being a beam which irradiates only a single row of detection elements, whereas a cone beam is preferentially regarded as being a beam which irradiates several adjacent rows of detection elements, especially all rows of detection elements. Thus, if only some rows are irradiated by fan beams only, in between the irradiated rows of detection elements non-irradiated rows of detection elements are preferentially present.

For instance, the radiation source may be adapted such that only a first, a last and an intermediate row of detection elements are irradiated. In particular, if the radiation source is rotatable with respect to the living being around a rotational axis, for instance, if the projection data providing unit is a projection data acquisition unit of a CT system, the several rows of detection elements may be arranged at different positions along the rotational axis, wherein the radiation source may comprise a collimator for collimating the radiation such that only the first, last and intermediate rows of detection elements are irradiated, wherein the terms "first", "last" and "intermediate" refer to the arrangement of the rows along the rotational axis and wherein the intermediate row is preferentially the central row. In this example the collimator generates several fan beams from an original cone beam. This can allow for an accurate determination of the FFR value with a reduced radiation dose. The radiation source and the living being may be arranged such that the projection data used for determining the boundary condition are generated based on the intensity of the fan beams after having traversed the ascending aorta.

In an embodiment the projection data providing unit is adapted to provide fan beam projection data having been generated by the detector over time based on radiation, which is generated by the radiation source and which has traversed the aorta at different locations, while a contrast agent has flown through the aorta from one of the different locations to another of the different locations, wherein the boundary condition determination unit is adapted to determine the boundary condition based on the provided projection data. The different locations preferentially include a location in the ascending aorta and a location in the descending aorta.

In an embodiment the representation providing unit is adapted to further provide a representation of the aorta showing the aorta between the different locations, wherein the boundary condition determination unit is adapted to determine the boundary condition based on the provided projection data and the representation of the aorta. For instance, the time needed by the contrast agent for flowing from one location of the aorta to another location of the aorta, which is obtainable from the projection data, can be used together with the distance along the aorta between these two locations, which is obtainable from the representation of the aorta, for determining the flow velocity within the aorta as a boundary condition. This allows for a determination of a boundary condition like a flow velocity within the aorta by using a single fan beam only, thereby allowing for a further reduced radiation dose applied to the living being.

In an embodiment the boundary condition determination unit is adapted to reconstruct an image showing the coronary artery system and surrounding regions, which surround vessels of the coronary artery system, over time based on the provided projection data and to determine an amount of blood leaving the coronary artery system based on the image as the boundary condition. Determining the amount of blood leaving the coronary artery system as the boundary condition and using this leaving blood for determining the FFR value can further improve the accuracy of determining the FFR value.

The boundary condition determination unit may be adapted to determine the amount of blood leaving the coronary artery system based on image values of image elements showing the surrounding regions. The image values may be indicative of the contrast level such that the amount of blood leaving the coronary artery system may be determined based on the contrast level in the surrounding regions. In particular, the boundary condition determination unit may be adapted to determine a myocardial tissue value being indicative of an uptake of a part of the contrast agent in the myocardial tissue based on the image values of the image elements showing the surrounding regions and to determine the amount of blood leaving the coronary artery system based on the myocardial tissue value. For instance, the difference of the Hounsfield unit (HU) value in the image region showing tissue surrounding a vessel of the coronary artery system in comparison to a muscle HU reference value can be used for determining, i.e. estimating, an amount of blood that flows outside the vessel.

In a further preferred embodiment the boundary condition determination unit is adapted to determine which image elements showing the surrounding regions represent side branches of the vessels of the coronary artery system, which are too small for being represented by the provided representation of the coronary artery system, based on the image values of the image elements showing the surrounding regions and to determine the amount of blood leaving the coronary artery system through the side branches based on the determined image elements. In particular, the boundary condition determination unit is adapted to compare image values of image elements showing the inside of a vessel with image values of the image elements showing the surrounding regions and to determine the image elements representing the side branches based on this comparison. Moreover, the boundary condition determination unit may be adapted to determine the dimensions of the side branches, which are too small for being represented by the provided representation of the coronary artery system, based on the determined image elements representing the side branches, and to determine the amount of blood leaving the coronary artery system through the side branches based on the determined dimensions. Thus, for instance, small side branches previously missed by a segmentation algorithm may be detected. All image elements, i.e. voxels, in the close neighborhood of the surface of the respective vessel may be evaluated with respect to their HU value in relation to the contrast agent induced HU enhancement inside the respective vessel, in order to account for variable contrast agent concentrations along the vessel. In case that the HU value is in a similar range as inside the vessel the enhancement outside the segmented structure may be a small side branch and its shape/diameter may be estimated. The side branch detection may be performed for different segments of the coronary artery system and side branch areas of different segments may be summed up and taken as an additional correction factor to estimate blood flowing out of the coronary artery tree at each vascular segment.

The boundary conditions determined by the boundary condition determination unit may be inflow and/or outflow boundary conditions at the inflow and/or outflow, respectively, of the coronary artery system. In particular, the boundary condition determination unit may be adapted to determine a flow velocity and optionally also dimensions of the coronary arteries at the outlets of the coronary artery system as a boundary condition. For instance, the boundary condition determination unit can be adapted to determine the flow velocity based on provided projection data by using known projection data based flow velocity determination algorithms like the algorithms disclosed in the article "CT angiographic measurement of vascular blood flow velocity by using projection data" by S. Prevrhal et al., Radiology, volume 261, number 3, pages 923 to 929 (2011) and in US 2011/027433310 A1, which are herewith incorporated by reference, wherein as an input for these algorithms not projection data of all rows of detection elements are used, but only projection data of some rows, especially of a first, a last and an intermediate row of detection elements. Moreover, the boundary condition determination unit may be adapted to determine the dimensions of the coronary arteries at the outlets of the coronary artery system based on the provided representation of the coronary artery system.

In an embodiment the apparatus further comprises a property providing unit for providing anatomical and/or physiological properties of the living being, wherein the boundary condition determination unit is adapted to determine the boundary condition based on the provided properties of the living being. The apparatus preferentially further comprises an assignments providing unit for providing assignments between anatomical and/or physiological properties and boundary conditions, wherein the boundary condition determination unit is adapted to determine the boundary condition based on the provided properties of the living being and the provided assignments. The assignments providing unit has preferentially been generated by using a machine learning algorithm, wherein the assignments providing unit is optimized such that deviations of calculated FFR values, which have been calculated by using boundary conditions that have been provided based on the provided properties and the assignments, from invasively measured FFR values are minimized. The property providing unit may be adapted to provide a cross-section area of a vessel of the coronary artery system and/or a myocardial mass and/or a ratio of diameters of a vessel and its branch of the coronary artery system and/or the heart size and/or the ejection fraction of the heart and/or the stroke volume of the heart as the property. Determining the boundary condition based on these provided properties can lead to a further improved accuracy of the finally determined FFR value.

The fractional flow reserve value determination unit may be adapted to use an FFR value determination algorithm that is based on a lumped model describing the flow within the coronary artery system, wherein the boundary condition determination unit is adapted to determine parameters of the lumped model as the boundary condition. In particular, the fractional flow reserve value determination unit may be adapted such that the lumped model describes the flow within the coronary system by using a combination of resistances and compliances, wherein a boundary condition may include a resistance and/or a compliance. For instance, a microvascular resistance can be determined based on a myocardial mass and a cross-section area of a vessel of the coronary artery system as a boundary condition. Using the lumped model for determining the FFR value can lead to an even further improved accuracy of the finally determined FFR value.

In another aspect of the present invention a method for determining an FFR value of the coronary artery system of a living being is presented, wherein the method comprises:
  providing a representation of the coronary artery system by a representation providing unit,
  determining the FFR value by using an FFR value determination algorithm that is configured to determine the FFR value based on a boundary condition and the provided representation of the coronary artery system by a fractional flow reserve value determination unit,
  providing projection data having been generated by a detector over time based on radiation, which is generated by a radiation source and which has traversed the aorta of the living being, while a contrast agent has flown through the aorta, by a projection data providing unit, wherein the detector has several rows of detection elements used for generating the projection data and wherein the radiation source is adapted such that not all rows of detection elements are irradiated, but only one row is irradiated by a single fan beam or some rows are irradiated by several fan beams,
  determining a boundary condition which is specific for the living being by a boundary condition determination unit based on the provided projection data.

In a further aspect of the present invention a computer program for determining an FFR value of the coronary artery system of a living being is presented, wherein the computer program comprises program code means for causing an apparatus as defined in claim 1 to carry out the steps of the method as defined in claim 12, when the computer program is run on a computer controlling the apparatus.

It shall be understood that the apparatus of claim 1, the method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
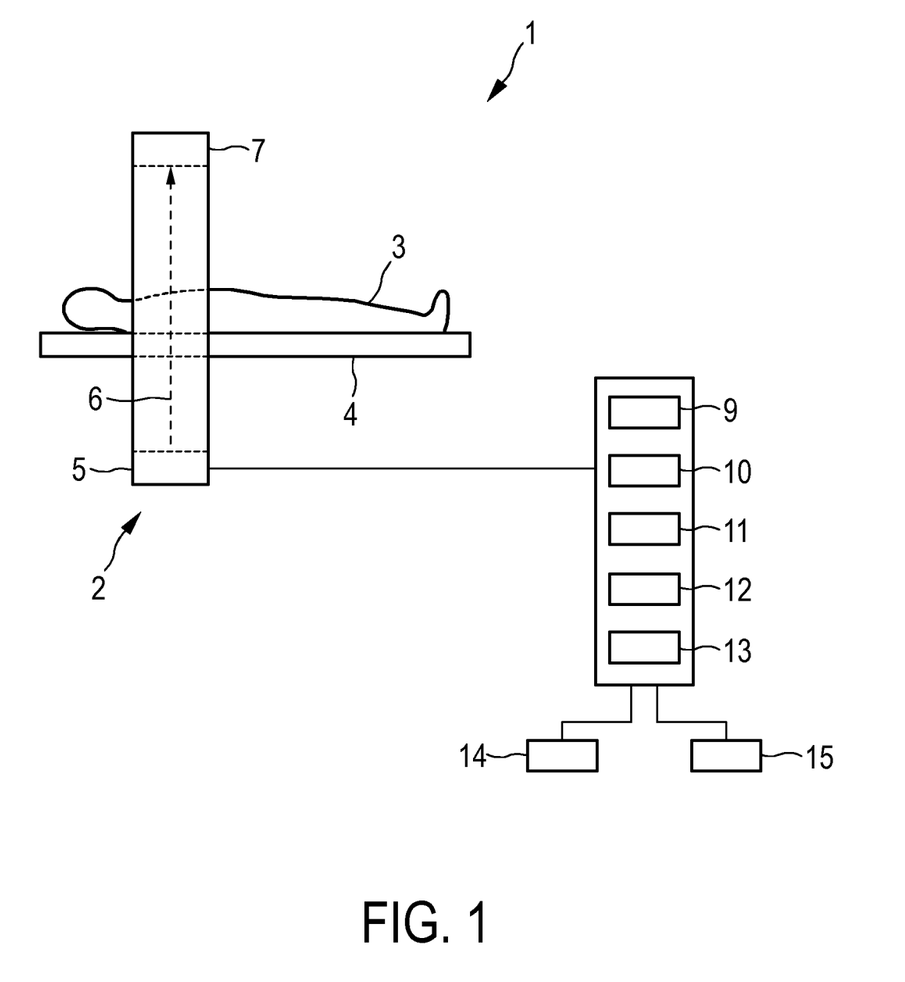
FIG. 1 shows schematically and exemplarily an apparatus for determining an FFR value of the coronary artery system of a living being, FIG. 2 schematically and exemplarily shows three fan beams, which may be used by the apparatus shown in FIG. 1 for determining the FFR value, FIG. 3 schematically and exemplarily shows locations in the ascending and descending aorta, FIG. 4 schematically and exemplarily shows a vessel of the coronary artery system and a surrounding soft tissue region.

FIG. 1 shows schematically and exemplarily an embodiment of an apparatus for determining an FFR value of the coronary artery system of a person. In this embodiment the apparatus 1 comprises a projection data providing unit 2 for providing projection data having been generated by a detector 7 over time based on radiation 6, which is generated by a radiation source 5 and which has traversed the aorta of the person 3 lying on a support means 4 like a table, while a contrast agent has flown through the aorta. The projection data providing unit 2 is preferentially an acquisition unit of a CT system. The apparatus 1 can therefore also be regarded as being a CT system which is adapted to determine the FFR value of the coronary artery system of the person 3.

The apparatus 1 further comprises a representation providing unit 9 for providing a representation of the coronary artery system. In this embodiment the representation providing unit 9 is adapted to reconstruct a CT image showing the coronary artery system based on projection data acquired by the projection data providing unit 2 in different acquisition directions and to segment the coronary artery system in the reconstructed CT image, in order to provide the representation of the coronary artery system. The representation providing unit 9 may be adapted to use, for instance, a model-based segmentation approach, a region growing or wave propagation method or an interactive coronary artery segmentation technique for segmenting the coronary artery system. The representation is preferentially a three-dimensional representation of the coronary artery system.

The apparatus 1 further comprises a boundary condition determination unit 12 for determining a boundary condition, which is specific for the person 3, and a fractional flow reserve value determination unit 13 for determining the FFR value by using an FFR value determination algorithm that it adapted to determine the FFR value based on the boundary condition and the representation of the coronary artery system. In particular, the fractional flow reserve value determination unit 13 may be adapted to simulate the flow of blood within the coronary artery system based on the representation of the coronary artery system and based on the boundary condition and to determine the FFR value based on the simulated flow of the blood, wherein the FFR value can be determined such that it is indicative of a blood pressure drop across an artery-narrowing stenosis. Thus, the FFR value determination algorithm is preferentially adapted to simulate the flow of blood within the coronary artery system. Simulation techniques are disclosed, for instance, in the articles "Diagnosis of ischemia-causing coronary stenoses by noninvasive fractional flow reserve computed from coronary computed tomographic angiograms. Results from the prospective multicenter DISCOVER-FLOW (Diagnosis of Ischemia-Causing Stenoses Obtained Via Noninvasive Fractional Flow Reserve) study" by B. K. Koo et al., Journal of the American College of Cardiology, 58 (19), pages 1989 to 1997 (2011), "Patient-specific modeling of blood flow and pressure in human coronary arteries" by H. J. Kim et al, Annals of Biomedical Engineering 38(10), pages 3195 to 3209 (2010), and "Outflow boundary conditions for three-dimensional simulations of non-periodic blood flow and pressure fields in deformable arteries" by I. E. Vignon-Clementel et al., 13(5), pages 625 to 640 (2010), which are herewith incorporated by reference.

The apparatus 1 further comprises an input unit 14 like a keyboard, a computer mouse, a touch pad, et cetera for allowing a user to input commands like a start command or a stop command into the apparatus 1, or to set parameters defining, for instance, the acquisition of projection data, the segmentation of the coronary artery system, the determination of the boundary conditions, the determination of the FFR values, et cetera. The apparatus 1 also comprises an output unit 15 like a monitor for showing, for instance, a generated CT image of the heart, the provided representation of the coronary artery system, an FFR value, et cetera.

Figure 2:
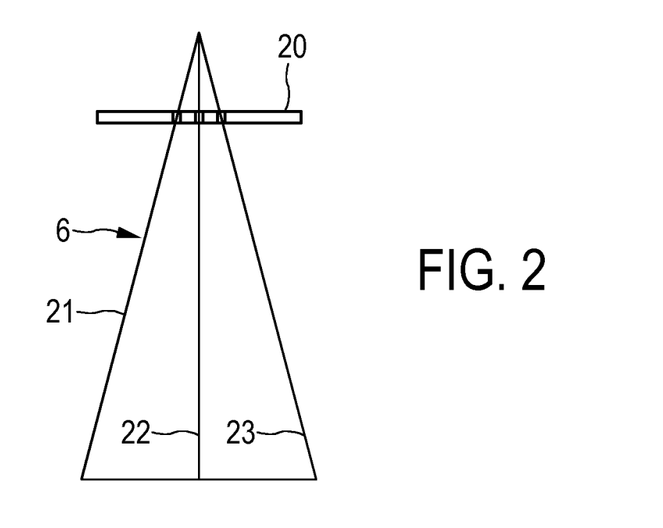

In this embodiment the radiation source 5 comprises a collimator 20 schematically and exemplarily illustrated in FIG. 2. The collimator 20 is adapted to generate three fan beams 21, 22, 23, wherein the radiation source 5 with the collimator 20 and the detector 7 are adapted such that the fan beams 21, 22, 23 irradiate a first row of detection elements of the detector 7, a last row of detection elements of the detector 7 and a central row of detection elements of the detector 7, wherein the terms "first", "last" and "intermediate" refer to the arrangement of the rows of the detection elements along the rotational axis of the rotational movement of the radiation source 5 and the detector 7 around the person 3. This rotational axis corresponds to the longitudinal axis of the projection data providing unit 2 and the longitudinal axis of the person 3.

The boundary condition determination unit 12 is adapted to determine, for instance, the flow velocity within the aorta as a boundary condition based on the provided projection data by using known projection data based flow velocity determination algorithms like the algorithms disclosed in the above mentioned article by S. Prevrhal et al. and the algorithms disclosed in US 2011/027433310 A1, wherein as an input for these algorithms not projection data of all rows of detection elements are used, but only projection data of the first, the last and the intermediate rows of detection elements.

Determining FFR values of the coronary arteries based on CT angiography imaging critically depends on the accuracy of modeling the coronary blood in- and outflow conditions.

The boundary condition determination unit 12 and the fractional flow reserve value determination unit 13 are therefore preferentially adapted to accurately determine the aortic blood flow velocity, in order to estimate inflow conditions and in order to finally derive more accurate FFR values.

An FFR value of the coronary artery system may be defined as the blood pressure drop across an artery-narrowing stenosis. The FFR value can be an important predictor of vascular health and is typically measured invasively in a catheterization laboratory during PCIs. The fractional flow reserve value determination unit 13 is preferentially adapted to simulate arterial fluid dynamics and to determine FFR values based on the provided representation of the coronary artery system, which is preferentially a coronary CT angiography (CCTA) representation of a single phase of the cardiac cycle, in order to determine the FFR values non-invasively. These non-invasively determined FFR values may be used as an additional functional parameter next to a spatial measurement of a degree of stenosis, in order to screen and triage persons to PCI by using CCTA. The fractional flow reserve value determination unit 13 is preferentially adapted to use the provided representation of the coronary artery system, which is preferentially a segmentation of the coronary artery tree obtained by segmenting a cardiac CT data set of the person 3, for simulating the blood flow velocity and pressure distribution in a vascular subsystem containing the stenosis.

In addition to the vascular anatomy, the simulation critically depends on the blood flow and pressure conditions of in- and outlet boundaries of the coronary tree. The fractional flow reserve value determination unit 13 is therefore adapted to additionally use the boundary conditions determined by the boundary condition determination unit 12 for simulating the blood flow velocity and pressure distribution in the vascular subsystem containing the stenosis. The projection data providing unit 2 is preferentially adapted to perform a standard protocol for single-phase CCTA, which includes a bolus timing scan. The bolus timing scan is a very low-dose, dynamic CT scan acquired prior to an actual CT angiography scan, in order to obtain a person specific time delay between a venous injection of CT contrast media and a peak saturation of the contrast at the heart. This delay is generally used to correctly time an actual CT angiography scan. The boundary condition determination unit 12 may be adapted to obtain aortic flow conditions as boundary conditions from the bolus timing scan.

For performing the bolus timing scan a small amount of contrast agent of, for instance, 10 to 20 ml may be injected into an arm vein of the person at a flow rate which is similar to the flow rate planned for the later coronary angiography scan, wherein optionally the injection may be followed by a saline chaser bolus. The flow rate might be within a range of 4 to 6 ml/s. However, also another flow rate might be used. Then, a CT image, especially a single slice CT image, of a target imaging area within the heart may be generated at equidistant time intervals, for example every second. The contrast in a vessel, especially in a major vessel like the aorta, in the CT image can be determined over time and, once the enhancement in the vessel has reached a contrast level, particularly a certain HU level, it can be assumed that the contrast bolus has arrived. The time can be measured, stored and used as a delay to start the actual CT angiography scan automatically when the full bolus arrives.

In order to determine, for instance, the blood flow at the in- and/or outlet boundaries of the coronary artery system, a flow velocimetry technique as disclosed in the above mentioned article by S. Prevrhal or as disclosed in US 2011/027433310 A1 may be used, wherein instead of using projection data of all rows of detection elements only projection data, i.e. the corresponding dynamic fan beam projection sequences, of the first, last and intermediate row of detection elements may be analyzed. For determining this flow velocity the projection data are preferentially acquired at the position of the ascending aorta.

In an embodiment the radiation source 5 may not irradiate the person 3 and the detector 7 by using several fan beams or by using a cone beam, but the radiation source 5 may be adapted to irradiate the person 3 and the detector 7 by a single fan beam only, in order to determine the boundary conditions. In particular, the projection data providing unit 2 may be adapted to provide single fan beam projection data having been generated by the detector 7 over time based on the radiation 6, which is generated by the radiation source 5 as a single fan beam in this embodiment and which has traversed different locations 30, 31 in the ascending and descending aortas, which are schematically and exemplarily shown in FIG. 3, wherein the boundary condition determination unit 12 can be adapted to determine a boundary condition, especially the flow velocities at the locations 30, 31 in the ascending and descending aorta, based on the provided projection data. Preferentially, the representation providing unit 9 is adapted to further provide a representation of the aorta showing the aorta between the different locations 30, 31, wherein the boundary condition determination unit 12 may be adapted to determine the boundary condition based on the provided projection data and the representation of the aorta. For instance, the time needed by the contrast agent for flowing from one location of the aorta to the other location of the aorta, which is obtainable from the projection data, can be used together with a distance along the aorta between these two locations, which is obtainable from the representation of the aorta, for determining the flow velocity as a boundary condition. Thus, data can be acquired at two distinct spatial positions 30, 31 within a single fan beam, wherein this single fan beam covers the ascending aorta and the descending aorta. Moreover, the three-dimensional length and shape of the aorta between these two measurement positions as well as the size of the carotid artery ostium may be estimated from the representation provided by the representation providing unit 9, which may be a segmented gated cardiac CT image, if these elements are covered, or these data may be obtained from, for instance, a scanogram acquired for planning a cardiac CT scan. The determined flow of blood between these two locations 30, 31 can be used as a boundary condition, while simulating the blood flow velocity and pressure distribution within the coronary artery system by the fractional flow reserve value determination unit 13.

Figure 3:
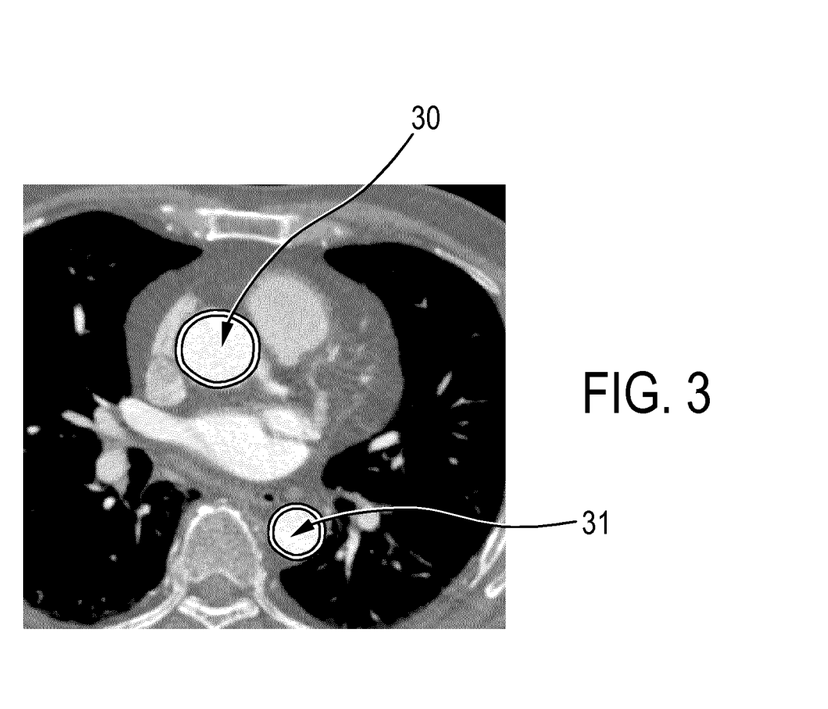

Thus, the arrival time difference of a bolus between the cross sections 30, 31 of the ascending and descending aorta can be put in relation with the distance between the two cross sections 30, 31 along the aortic arch and also with their sizes, in order to derive a volumetric blood flow. The arrival time difference is determined by using projection data, which are acquired, for instance, at an about 1000-fold faster rate than the reconstructed images and which therefore offer an amply sufficient temporal resolution for the proposed measurement, i.e. the blood flow velocity during the systole may be of the order of 40 to 80 cm/s and the aortic arch may span about 5 cm, which yields an upper limit of only about 0.1 s for the bolus arrival time difference, wherein this small bolus arrival time difference can accurately be determined by using the acquired projection data.

Coronary imaging is important for diagnosis and decision making in cases of coronary heart disease. A treatment may be needed, if a coronary function is impaired by stenosis. A CCTA examination is a non-invasive, relatively low-dosed tool to screen persons in need of PCI. An FFR value is a very good predictive value for treatment decisions and it is therefore desirable to measure it during a CCTA examination by simulating the blood flow. The boundary conditions critically drive the simulation. The apparatus described above with reference to FIG. 1 therefore models, i.e. determines, these boundary conditions in an accurate way, preferentially without expending additional radiation dose to the person. The apparatus preferentially uses the bolus timing scan, which is already a necessary part of a standard CCTA scan protocol. The blood velocity and derived quantities like a time-to-peak enhancement may be visualized in color coded images, wherein the color-coded images may show the coronary artery system and the aorta, wherein different colors may indicate different blood flow velocities and optionally other derived quantities.

In a further embodiment the boundary condition determination unit 12 may be adapted to reconstruct an image showing the coronary artery system and surrounding regions, which surround vessels of the coronary artery system, over time based on the provided projection data and to determine an amount of blood leaving the coronary artery system based on the image as a boundary condition. In particular, the boundary condition determination unit can be adapted to determine the amount of blood leaving the coronary artery system based on image values of image elements showing the surrounding regions. The image values may be indicative of the contrast level such that the amount of blood leaving the coronary artery system may be determined based on the contrast level in the surrounding regions.

The boundary condition determination unit 12 may be adapted to determine a myocardial tissue value being indicative of an uptake of a part of the contrast agent in the myocardial tissue based on the image values of the image elements showing the surrounding regions and to determine the amount of blood leaving the coronary artery system based on the myocardial tissue value. For instance, the difference of the HU value in the image region showing tissue surrounding a vessel of the coronary artery system in comparison to a muscle HU reference value can be used for determining, i.e. estimating, an amount of blood that flows outside the vessel. For example, the number of voxels in the surrounding region, which have a HU value indicating a stronger contrast than the muscle tissue, may be determined, wherein the boundary condition determination unit 12 may be calibrated such that this number of voxels yields the respective contrast agent uptake in the myocardial tissue. In particular, the number of voxels may be multiplied with a calibration factor for determining the respective contrast agent uptake in the myocardial tissue. The fractional flow reserve value determination unit 13 may be adapted to consider the determined amount of blood leaving the coronary artery system while simulating the blood flow velocity and pressure distribution within the coronary artery system.

In an embodiment regions of voxels can be defined around each artery, a baseline intensity of, for instance, 50 HU can be subtracted from each voxel enhancement, and the total enhancement in a region can be calculated as the sum of voxel enhancements after subtraction. This total enhancement can be compared for different artery regions, and the ratio of sums of enhancements can be used for indicating the ratio of blood and contrast agent flowing through the respective arteries. The ratio can be used as a boundary condition during the simulation of the fluid dynamics.

The boundary condition determination unit 12 can also be adapted to determine which image elements showing the surrounding regions represent side branches of the vessels of the coronary artery system, which are too small for being represented by the provided representation of the coronary artery system, based on the image values of the image elements showing the surrounding regions and to determine the amount of blood leaving the coronary artery system through the side branches based on the determined image elements. For example, the boundary condition determination unit 12 can be adapted to compare image values of image elements showing the inside of a vessel with image values of the image elements showing the surrounding regions and to determine the image elements representing the side branches based on this comparison. Moreover, the boundary condition determination unit 12 may be adapted to determine the dimensions of the side branches, which are too small for being represented by the provided representation of the coronary artery system, based on the determined image elements representing the side branches, and to determine the amount of blood leaving the coronary artery system through the side branches based on the determined dimensions.

Thus, small side branches previously missed by a segmentation algorithm may be detected, wherein all image elements, i.e. all voxels, in the close neighborhood of the surface of the respective vessel may be evaluated with respect to their HU value in relation to the contrast agent induced HU enhancement inside the vessel, in order to account for variable contrast agent concentrations along the vessel. In case that the HU value is in a similar range as inside the vessel the enhancement outside the segmented structure is a small side branch and its shape/diameter can be estimated. The side branch detection can be performed for different segments of the coronary artery system and side branch areas of different segments can be summed up and taken as an additional correction factor to estimate blood flowing out of the coronary artery tree at each vascular segment. The side branch areas may be excluded from the tissue analysis described above, i.e. the tissue uptake quantification may only be applied to voxels which have not been classified as side branches, because it is preferentially assumed that each voxel represents one of the three categories vessel, side branch and tissue. The estimated blood flowing out of the coronary artery tree at each vascular segment can be used as a boundary condition for determining the fractional flow reserve value.

The representation providing unit 9 is preferentially adapted to provide a segmentation of a coronary artery tree, which is used by the fractional flow reserve value determination unit 13 for calculating coronary FFR values based on computational fluid dynamics or lumped simulations. A factor that influences the accuracy and quality of the FFR calculation is the accuracy of estimating the amount of contrast agent, i.e. the amount of blood, leaving each coronary artery segment. However, the segmentation provided by the representation providing unit 9 can segment the vessels, particularly the main vessel tree, only up to a predetermined vessel size, which is defined by the segmentation algorithm and the quality of the original image of the coronary artery system, which is used for the segmentation. Only vessel pieces which are explicitly segmented can generally serve as an outlet of blood out of the main coronary tree during the simulation performed by the fractional flow reserve value determination unit 13. Known FFR simulation approaches do not consider smaller vessel pieces, which are not segmented, and they assume that the coronary tree is sealed except of the inlets and outlets, which is not correct. Thus, as described above, the boundary determination unit 12 may be adapted to estimate the amount of blood leaving the coronary artery system through the myocardial tissue and through side branches, which have not been segmented, especially for each piece, i.e. segment, of the coronary artery tree. In particular, the boundary condition determination unit 12 may be adapted to estimate the amount of blood leaving each coronary artery segment based on the myocardial tissue enhancement in the proximity of the coronary artery tree, in order to better constrain the boundary conditions for the FFR simulation, wherein for estimating the boundary conditions image information of a CT angiography data set is preferentially used.

Figure 4:
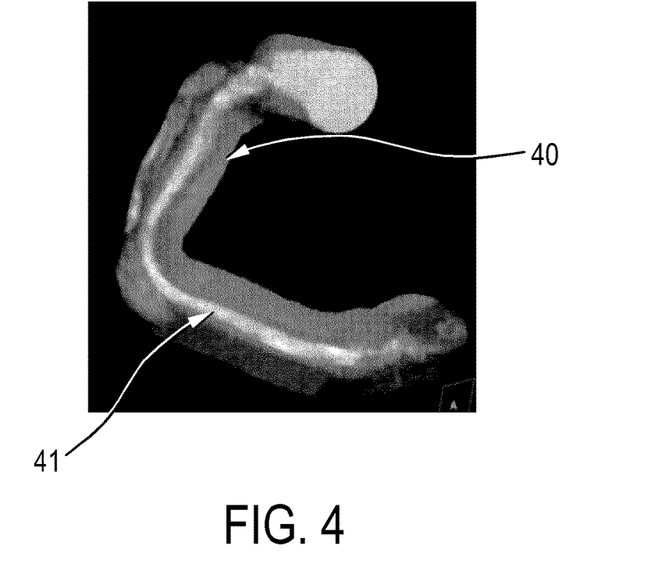

For estimating the outflow boundary conditions accurately the segmented surface of the respective vessel of the coronary artery system can be used as a starting point, wherein the contrast level in a tissue region 40 surrounding the vessel 41, which is schematically and exemplarily illustrated in FIG. 4, may be determined. The vessel 41 is a right coronary artery of the coronary artery system, wherein the tissue region of interest 40 surrounding the vessel is a 10 mm radius region of interest and wherein FIG. 4 shows a maximum intensity projection visualization. The difference of the HU value in the surrounding tissue 40 in comparison to a muscle HU reference value taken from literature or from a reference muscle area in this data set may be determined, wherein the mean enhancement may deliver an indication about the amount of blood that flows outside the vessel 41, which may be regarded as being a main vessel in this example. This indication about the amount of blood that flows outside the main vessel can be regarded as being a boundary condition, which can be used by the fractional flow reserve value determination unit 13 for accurately estimating the flow distribution in the coronary artery tree, which in turn leads to an improved determination of the FFR values. As a further boundary condition the vessel size at the outlets of the tree as obtainable from the provided representation of the coronary artery system can be used by the fractional flow reserve value determination unit 13.

The projection data providing unit 2 may be a projection data acquisition unit of a dual energy CT scanner, wherein the dual energy CT scanner can be adapted to generate a contrast agent image just showing the contrast agent and indicating the quantity of the contrast agent, which might be iodine, especially in the vicinity of a respective coronary artery. Using such a dual energy CT scanner can further improve the accuracy of determining the blood flowing out of the coronary artery system as a boundary condition.

Figure 5:
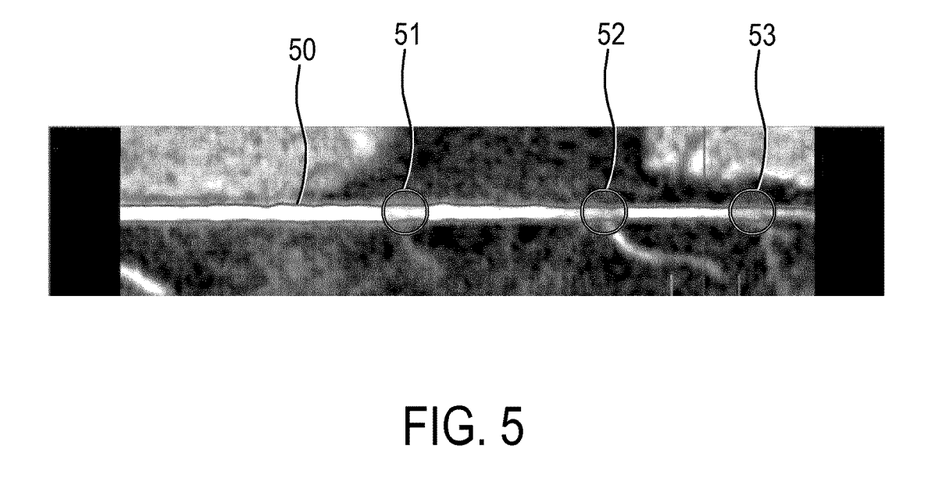
FIG. 5 schematically and exemplarily shows locations, which include small side branches, of a vessel of the coronary artery system, FIG. 6 schematically and exemplarily illustrates a lumped model which may be used for determining the FFR value, FIG. 7 schematically and exemplarily illustrates an optimization process for generating assignments between a) anatomical and/or physiological properties and b) boundary conditions.

Using the additional information, i.e. the boundary conditions, in comparison to a pure vascular model currently used in FFR simulation can improve the accuracy of the calculation of the FFR values. Moreover, the virtual FFR determination technique may be easier to use for a radiologist, because an initial segmentation of the coronary arteries may be restricted to the major vessels, wherein the smaller vessels can be considered by determining the blood flowing out of the coronary artery system as described above, i.e. missing side branches will be automatically integrated using the above described modifications by using corresponding boundary conditions during the simulation of the velocity and pressure distribution within the coronary artery system. FIG. 5 schematically and exemplarily illustrates a reformatted view of a volumetric CT angiography data set, which may be generated by the apparatus 1 shown in FIG. 1, wherein a main vessel 50 of the coronary system and regions 51, 52, 53 are presented, for which small side branches have been determined by the boundary condition determination unit 12, which were not included in the segmentation of the main vessel 50.

The apparatus 1 may further comprise a property providing unit 10 for providing anatomical and/or physiological properties of the person 3, wherein the boundary condition determination unit 12 may be adapted to determine the boundary condition based on the provided properties of the person 3. The provided properties are preferentially a cross-section area of a vessel of the coronary artery system, a myocardial mass, a ratio of diameters of a vessel and its branch of the coronary artery system, a heart size, an ejection fraction of the heart and/or a stroke volume of the heart. The apparatus 1 preferentially further comprises an assignments providing unit 11 for providing assignments between these properties and boundary conditions, wherein the boundary condition determination unit 12 may be adapted to determine the boundary condition based on the provided properties of the person 3 and the provided assignments. The assignments have preferentially been generated by using a machine learning algorithm, wherein the assignments are optimized such that deviations of calculated FFR values, which have been calculated by using boundary conditions that have been provided based on the provided properties and the assignments, and measured FFR values are minimized.

In an embodiment the fractional flow reserve value determination unit 13 may be adapted to use an FFR value determination algorithm that is based on a lumped model describing the flow within the coronary artery system, wherein the boundary condition determination unit 12 may be adapted to determine parameters of the lumped model as the boundary condition. In particular, the fractional flow reserve value determination unit 13 may be adapted such that the lumped model describes the flow within the coronary artery system by using a combination of resistances and compliances, wherein a boundary condition may be a resistance and/or a compliance. For instance, a microvascular resistance can be determined based on a myocardial mass and a cross-section area of a vessel of the coronary artery system.

Generally FFR values are determined by using an invasive technique including coronary catheterization, in order to measure pressure differences across a coronary artery stenosis, wherein this narrowing is generally caused by atherosclerosis. The FFR value is generally determined, in order to estimate the likelihood that the stenosis impedes oxygen delivery to the heart muscle, i.e. to estimate the likelihood of myocardial ischemia. The FFR value may be defined as the pressure behind, i.e. distal to, a stenosis relative to the proximal pressure before the stenosis. The FFR value can be, for instance, an absolute number, which may be between zero and one. For example, an FFR value of 0.50 may mean that a given stenosis causes a 50 percent drop in blood pressure. In other words, an FFR value may express the maximal flow down a vessel in the presence of a stenosis compared to the maximal flow in the hypothetical absence of the stenosis.

During invasive coronary catheterization a catheter is inserted into the femoral or radial arteries using a sheath and a guidewire. A small sensor on the tip of the guidewire may be used for measuring the pressure, in order to determine the exact severity of the lesion. This is generally done during a maximal blood flow, i.e. during hyperemia, which may be induced by injecting vasodilator materials such as adenosine or papaverine. It is assumed that, if a PCI is performed for persons having an FFR value, which is lower than 0.8, the overall death and cardiac event rate will be lower in comparison to a regular decision making that is based on a percentage of a stenosis.

The apparatus 1 described above with reference to FIG. 1 can be adapted to estimate an FFR value using a computational fluid dynamics (CFD) simulation which is based on a coronary geometry, i.e. on the representation of the coronary artery system, obtained from a cardiac CT image. The determination of the FFR value may therefore also be regarded as being an FFR-CT determination. Estimating the FFR value based on CT studies allows for a non-invasive determination of valuable functional diagnostic information, which can be presented to a physician. In order to estimate the FFR value accurately, this estimation preferentially includes boundary conditions with respect to, for instance, the vessel anatomy and other anatomical and physiological features of a person as described above and as will also be described in the following. In particular, a machine learning approach can be used, in order to find a relation between lumped model parameters, which may be used for estimating an FFR value and which may be regarded as defining boundary conditions, and, for instance, a person's anatomical features.

Figure 6:
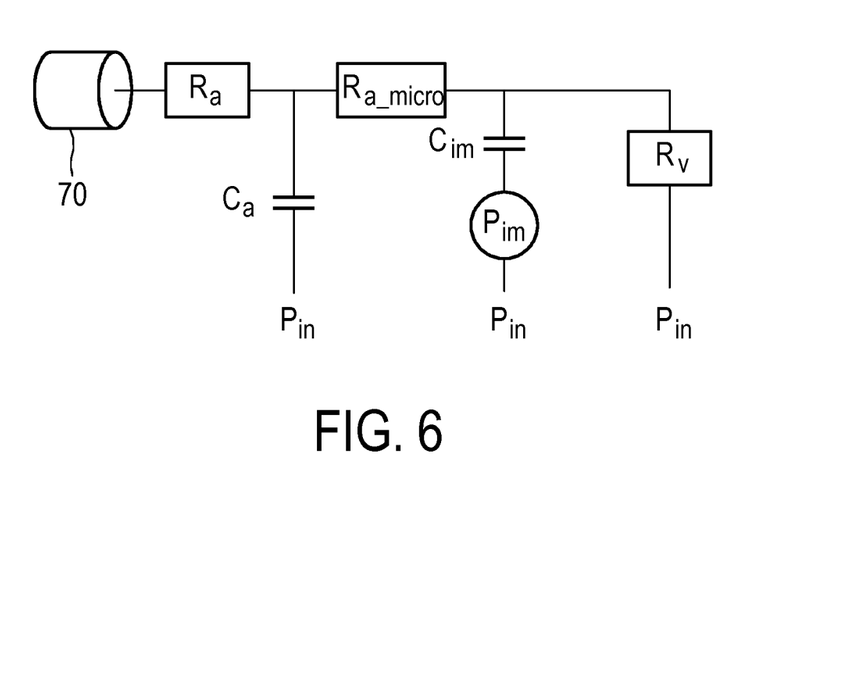

The fractional flow reserve value determination unit 13 may be adapted to use a lumped model for the left coronary branches, which is schematically and exemplarily illustrated in FIG. 6. In this example the lumped model comprises a vessel outlet 70, a coronary arterial resistance $R_a$, coronary arterial compliance $C_a$, a coronary arterial microcirculation resistance $R_{a\text{-}micro}$, a myocardial compliance $C_a$, a coronary venous resistance $R_v$, a dynamic intramyocardial pressure $P_{im}$ and a pressure $P_{in}$ in the inlets. By using this lumped model pressure values are estimated and the FFR value can be calculated from the lumped model estimation of the pressure along the coronaries by dividing the distal pressure by the pressure in the inlets. For more details regarding this lumped model approach reference is made to the article "Patient-specific modeling of blood flow and pressure in human coronary arteries" by H. J. Kim et al., Annals of Biomedical Engineering 38(10), pages 3195 to 3209 (2010), which is herewith incorporated by reference. This lumped model considers the influence by the contraction and relaxation of the heart. However, in another embodiment also other lumped models can be used for estimating FFR values in a person.

The parameters of the lumped model may vary from person to person such that the boundary condition determination unit 12 may be adapted to determine person specific parameters like a person specific microvascular resistance, for instance, the above mentioned coronary arterial microcirculation resistance, wherein the fractional flow reserve value determination unit 13 may be adapted to determine the FFR values based on the lumped model and the person specific parameters of the lumped model. In particular, the boundary condition determination unit 12 may be adapted to optimize person specific lumped model parameters based on anatomical and physiological features of the person, wherein an FFR-CT analysis may be performed based on the determined person specific boundary conditions, i.e. the person specific lumped model parameters.

In an embodiment the representation providing unit 9 may be adapted to segment vessels of a coronary artery system in a CT image, in order to generate a three-dimensional coronary structure as the representation of the coronary artery system. In particular, the representation providing unit 9 can be adapted to automatically extract vessel centerlines and lumina within the CT image, wherein the representation providing unit 9 can be further adapted to allow a user like a physician to interactively and manually edit the segmentation. The property providing unit 10 can be adapted to determine the diameter, especially the effective diameter, of the vessels based on the three-dimensional coronary structure, in order to provide an anatomical property of the person 3, wherein the effective diameter of a vessel in a certain cross section may be defined as being the diameter of a circle having the same area as the area of the vessel in the cross section.

The assignments providing unit 11 may be adapted to provide assignments relating anatomical/physiological features of the person 3 to the lumped model parameters, wherein the assignments can be used by the boundary condition determination unit 12 for determining lumped model parameters as boundary conditions based on anatomical/physiological features provided by the property providing unit 10. There may be several main optional relations between, for instance, the microvascular resistance as a lumped model parameter and anatomical features. For instance, a relation between anatomical features of a person and the microvascular resistance $R_{a\_micro}$ or another boundary condition parameter may be represented by using a parametric function. For example, the relation between a) the coronary arterial microcirculation resistance $R_{a\_micro}$ and b) a cross-sectional area CSA and a myocardial mass MyoMass may be defined by following parametric function:

$$R_{a\_micro} = A(\text{MyoMass})^{-1} + B(\text{CSA})^{-1} + C \quad (1)$$

wherein A, B and C are coefficients of the parametric function, which can be or have been optimized by a machine learning process which uses a training data set, in order to provide an assignment between a) the microvascular resistance and b) the person-specific cross-section area and the myocardial mass.

As a relation between flows in a vessel and its branch with respect to their diameters following equation may be provided:

$$Q = Q_0 \left(\frac{d}{d_0}\right)^{\frac{7}{3}}, \quad (2)$$

wherein Q defines the flow in the branch, $Q_0$ defines the flow in the vessel, d indicates the diameter of the branch and $d_0$ indicates the diameter of the vessel, wherein the flow may be defined as being the amount of fluid volume that passes through a lumen cross section during a time interval. Based on this relation a further relation can be derived, which describes the flow split of two branches based on their respective diameters:

$$\frac{Q_1}{Q_2} = \left(\frac{d_1}{d_0}\right)^{\frac{7}{3}}, \quad (3)$$

wherein $Q_1$ indicates the flow within a first branch, $Q_2$ indicates the flow within a second branch, $d_1$ indicates the diameter of the first branch and $d_2$ indicates the diameter of the second branch. Dividing this relation by the pressure before the bifurcation yields following relation between the resistances of the two branches with respect to the flow:

$$\frac{R_1}{R_2} = \left(\frac{d_1}{d_0}\right)^{-\frac{7}{3}}, \qquad (4)$$

wherein $R_1$ indicates the resistance of the first branch and $R_2$ indicates the resistance of the second branch. These resistances are likely dominant by peripheral microvascular arteries with a diameter lower than 0.2 mm. Another useful relation is the following one between velocities of two branches:

$$\frac{v_1}{v_2} = \left(\frac{d_1}{d_0}\right)^{\frac{1}{3}}, \qquad (5)$$

wherein $v_1$ indicates the velocity of the flow within the first branch and $v_2$ indicates the velocity within the second branch.

The relation between the thicknesses of the coronary arteries and the microvascular resistance is not fully unique. In addition, the thickness of an artery is fluctuating rather than constant. Therefore, the use of other anatomical features for estimating the coronary resistance and flow can also be beneficial. The myocardium is the destination of the coronary flow. It is therefore reasonable that an enlargement of the cardiac muscle with respect to the body demand will rise the generation of small blood vessels that will reduce the microvascular resistance and increase the flow. The relation between the myocardial mass and the microvascular resistance may improve the estimation of the resistance for a given person. Thus, in an embodiment the property providing unit 10 may provide at least the myocardial mass as a property and the assignments providing unit 11 may be adapted to provide assignments between the myocardial mass and the microvascular resistance, in order to determine the microvascular resistance of the lumped model based on the myocardial mass, wherein the determined microvascular resistance is determined by the boundary condition determination unit 12 as a boundary condition.

Moreover, it is assumed that the hyperemic microvascular resistance is higher in vessels with significant stenosis. This is supported by the effect of angioplasty which restores distal pressure and results in resistance values that do not significantly differ from values of normal vessels. A higher microvascular resistance may be explained by a vasoconstriction as a result of a passive collapse of larger-sized arterial microvessels due to reduced distending pressure. Other additional anatomical and physiological features, which may be provided by the property providing unit 10, could be the heart size or the ejection fraction or stroke volume. In general, there is a variability of the heart size, myocardial mass and artery diameters across persons. In an embodiment a person-specific model is therefore provided where one or several of these variables are used to estimate the person-specific vascular resistance rather than using a fixed resistance for all persons.

Persons with a reduced systolic/diastolic function may have different compression forces which may change the blood impedance, i.e. the resistance to the blood flow, in the systolic period. Therefore, given a large data set, the relations between the heart size or heart function parameters to the boundary conditions like blood impedances may improve the boundary condition estimate.

The assignments providing unit 11 is preferentially adapted to provide one or several parametric functions for assigning anatomical and/or physiological properties, which have been provided by the property providing unit 10, to boundary conditions, especially to parameters of the lumped model used for determining the FFR value. Preferentially, an optimizer is used for determining coefficients of the parametric function, wherein a training set is used, which comprises invasively measured FFR values and, for instance, corresponding representations of coronary artery systems, which can be used for calculating FFR values based on a blood flow distribution simulation. The optimizer is preferentially adapted to optimize the coefficients by minimizing the difference between the simulated FFR values and the measured FFR values of the training set. For this optimization process known optimizers can be used like optimizers which are based on a gradient descent optimization. A preferred optimization process, which can also be regarded as being a machine learning process, for determining coefficients of a parametric function defining the assignments between the anatomical and/or physiological properties and the boundary conditions will in the following be described with reference to FIG. 7.

Figure 7:
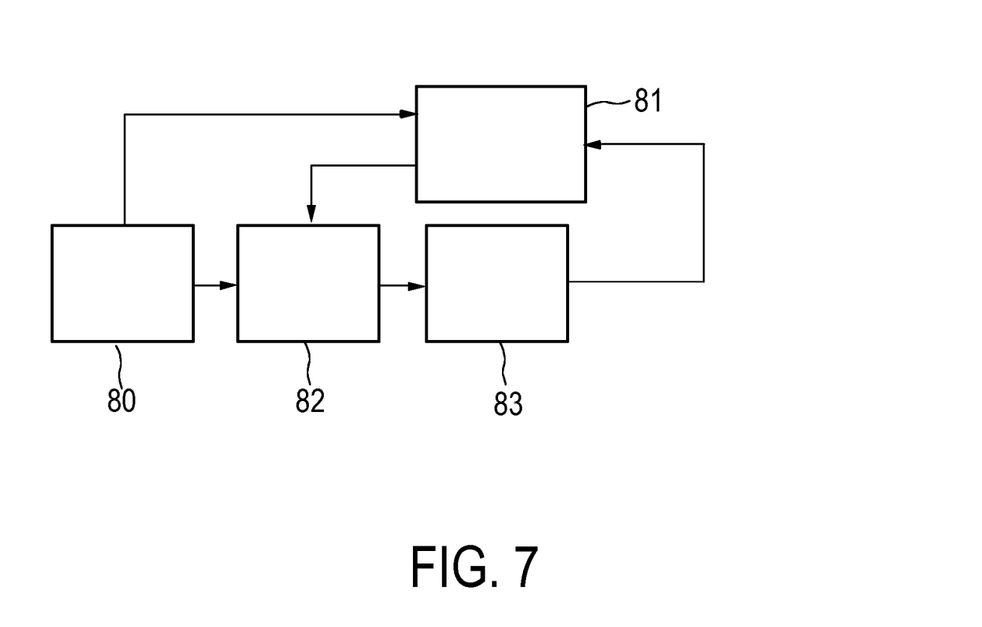

In this example the boundary condition is modeled by the total peripheral resistance to flow R, which may be described by following parametric function:

$$R = \frac{A(MayoMass)^{-1} + B}{CSA}, \qquad (6)$$

wherein the coefficients A and B need to be optimized by the optimization process. The property providing unit 10 calculates the branch cross-section area and the myocardial mass for each case in a training set 80 comprising representations of coronary artery systems and corresponding invasive FFR measurements. Then, the coefficients A, B are initialized and the boundary condition determination unit determines initial boundary conditions, i.e. in this example the total peripheral resistance R, based on the calculated cross-section area and myocardial mass, the initial coefficients and equation (6). Preferentially, the coefficients A, B are initialized such that the initial boundary condition is as close as possible to a literature value. Thus, in this example the coefficients A, B are initialized such that the total peripheral resistance R is as close as possible to a literature value given the calculated cross-section area and myocardial mass. In FIG. 7 this determination of the boundary condition is indicated by the box 82.

Then, an FFR value is determined by performing a CFD simulation, which is performed by the fractional flow reserve value determination unit 13. This determination of the FFR value is indicated in FIG. 7 by the box 83. As next steps, each coefficient is varied (A=A+dA and B=B+dB), the FFR value is determined again with the varied coefficients and the numerical derivative is determined:

$$\frac{dFFR}{dA} = \frac{FFR(A) - FFR(A + dA)}{dA} \text{ and} \qquad (7)$$

$$\frac{dFFR}{dB} = \frac{FFR(B) - FFR(B + dB)}{dB}. \qquad (8)$$

These numerical derivatives may be used to vary the coefficients A, B such that a deviation of the calculated FFR values from the invasively measured FFR values of the training set is minimized. For instance, a gradient descent approach can be applied, in order to minimize a sum of squared differences SSD(FFR$_{CT}$, FFR$_{measured}$) in accordance with following expressions:

$$A \leftarrow A - \text{step} \cdot (FFR_{CT} - FFR_{measured}) \frac{dFFR}{dA} \text{ and} \quad (9)$$

$$B \leftarrow B - \text{step} \cdot (FFR_{CT} - FFR_{measured}) \frac{dFFR}{dB}. \quad (10)$$

In these expressions FFR$_{CT}$ indicates the calculated FFR values and FFR$_{measured}$ indicates the invasively measured FFR values of the training set. The calculation of the numerical derivatives by using the gradient descent approach is denoted by the box 81 in FIG. 7.

Figure 8:
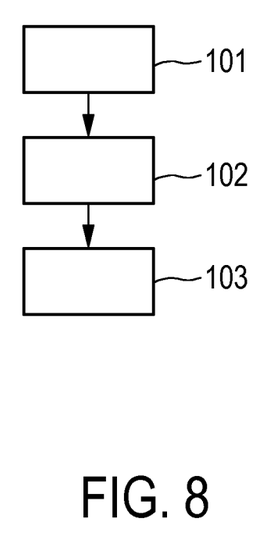
FIG. 8 shows a flowchart exemplarily illustrating an embodiment of a method for determining an FFR value of the coronary artery system of the living being.

In the following an embodiment of a method for determining an FFR value of a coronary artery system of a living being will exemplarily be described with reference to a flowchart shown in FIG. 8.

In step 101 a representation of the coronary artery system is provided by the representation providing unit 9. For instance, the coronary artery system is segmented in a CT image showing the coronary artery system. In step 102 boundary conditions, which are specific for the living being, are determined by the boundary condition determination unit 12. For instance, velocities of a flow into the coronary artery system, an amount of blood leaving the coronary arteries, the diameter of vessels at outflow locations and/or inflow locations, parameters of a lumped model, which may be used for determining the FFR value, may be determined as boundary conditions. In step 103 an FFR value is determined by using an FFR value determination algorithm that is configured to determine the FFR value based on the boundary conditions, which have been determined in step 102, and based on the provided representation of the coronary artery system by the fractional flow reserve value determination unit 13. In particular, the fractional flow reserve value determination unit 13 performs a simulation of a velocity and pressure distribution within the coronary artery system based on the representation of the coronary artery system and the boundary conditions, in order to determine an FFR value at a detected stenosis. The stenosis may be automatically detected by using a stenosis detection algorithm, wherein, for instance, the open diameter within the respective vessel as obtainable from the provided representation of the coronary artery system may be thresholded for detecting a stenosis. Also a graphical user interface may be provided for allowing a user to manually or semi-automatically indicate a stenosis, wherein the FFR value may be determined at the indicated stenosis.

The apparatus described above with reference to FIG. 1 allows for a non-invasive, accurate and objective estimation of an FFR value. This determination can be done in a fast and robust manner. The determined FFR value can then be used for assessing the physiologic significance of a coronary stenosis.

Although in the embodiment described above with reference to FIG. 1 the apparatus for determining the FFR value of the coronary artery system of the living being is a CT system, in another embodiment the apparatus for determining an FFR value of the coronary artery system may just be a computing system, wherein the computing system may receive, for instance, projection data from a separate projection data acquisition unit, a CT image from an external CT scanner, et cetera.

Although in above described embodiments the living being is a person, in other embodiments the apparatus can also be adapted to determine an FFR value of an animal.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of a boundary condition, the simulation of a velocity and pressure distribution, the determination of an FFR value, et cetera performed by one or several units or devices can be performed by any other number of units or devices. For example, steps 101 to 103 can be performed by a single unit or by any other number of different units. These operations and/or the control of the apparatus for determining an FFR value of the coronary artery system of a living being in accordance with the method for determining an FFR value of the coronary artery system of a living being can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for determining a fractional flow reserve value of the coronary artery system of a living being, the apparatus comprising:
   a representation providing unit for providing a representation of the coronary artery system;
   a projection data providing unit for providing projection data comprising:
      a radiation source configured to generate radiation during a contrast enhanced scan of an aorta of a living being,
      a detector configured to generate projection data based on the radiation, and
      a region between the radiation source and the detector with the living being disposed therein,
      wherein the detector has several rows of detection elements used for generating the projection data, and
      wherein the radiation source is adapted such that not all rows of the detection elements are irradiated, but only one row is irradiated by a single fan beam or at least one row is irradiated by several fan beams;
   a boundary condition determination unit for determining a boundary condition which is specific for the living being based on the provided projection data; and
   a fractional flow reserve value determination unit for determining the fractional flow reserve value by using a fractional flow reserve value determination algorithm that is adapted to determine the fractional flow reserve value based on the boundary condition and the provided representation of the coronary artery system.

2. The apparatus as defined in claim 1, wherein the projection data providing unit is adapted to provide fan beam projection data having been generated by the detector over time based on radiation, which is generated by the radiation source and which has traversed the aorta at different locations, while a contrast agent has flown through the aorta from one of the different locations to another of the different locations, wherein the boundary condition determination unit is adapted to determine the boundary condition based on the provided projection data.

3. The apparatus as defined in claim 2, wherein the representation providing unit is adapted to further provide a representation of the aorta showing the aorta between the different locations, wherein the boundary condition determination unit is adapted to determine the boundary condition based on the provided projection data and the representation of the aorta.

4. The apparatus as defined in claim 1, wherein the boundary condition determination unit is adapted to reconstruct an image showing the coronary artery system and surrounding regions, which surround vessels of the coronary artery system, over time based on the provided projection data and to determine an amount of blood leaving the coronary artery system based on the image as the boundary condition.

5. The apparatus as defined in claim 4, wherein the boundary condition determination unit is adapted to determine the amount of blood leaving the coronary artery system based on image values of image elements showing the surrounding regions.

6. The apparatus as defined in claim 5, wherein the boundary condition determination unit is adapted to determine a myocardial tissue value being indicative of an uptake of a part of a contrast agent in the myocardial tissue based on the image values of the image elements showing the surrounding regions and to determine the amount of blood leaving the coronary artery system based on the myocardial tissue value.

7. The apparatus as defined in claim 5, wherein the boundary condition determination unit is adapted to determine which image elements showing the surrounding regions represent side branches of the vessels of the coronary artery system, which are too small for being represented by the provided representation of the coronary artery system, based on the image values of the image elements showing the surrounding regions and to determine the amount of blood leaving the coronary artery system through the side branches based on the determined image elements.

8. The apparatus as defined in claim 1, wherein the boundary condition determination unit is adapted to determine a flow velocity and/or dimensions of the coronary arteries at the outlets of the coronary artery system as a boundary condition.

9. The apparatus as defined in claim 1, wherein the apparatus further comprises a property providing unit for providing anatomical and/or physiological properties of the living being, wherein the boundary condition determination unit is adapted to determine the boundary condition based on the provided properties of the living being.

10. The apparatus as defined in claim 9, wherein the property providing unit is adapted to provide a cross-section area of a vessel of the coronary artery system and/or a myocardial mass and/or a ratio of diameters of a vessel and its branch of the coronary artery system and/or the heart size and/or the ejection fraction of the heart and/or the stroke volume of the heart as the property.

11. The apparatus as defined in claim 1, wherein the fractional flow reserve value determination unit is adapted to use a fractional flow reserve value determination algorithm that is based on a lumped model describing the flow within the coronary artery system and wherein the boundary condition determination unit is adapted to determine parameters of the lumped model as the boundary condition.

12. A method for determining a fractional flow reserve value of the coronary artery system of a living being, the method comprising:
providing a representation of the coronary artery system by a representation providing unit;
generating a fan beam of radiation with a radiation source during a contrast enhanced scan of a vessel of a subject, wherein the fan beam traverses the vessel in an examination region;
receiving a single fan beam of the generated radiation traversing the vessel with only a single row of a multi-row detector or receiving a plurality of fan beams with a plurality of rows of the multi-row detector;
providing, with the multi-row the detector, projection data based on the received radiation;
determining a boundary condition which is specific for the living being by a boundary condition determination unit based on the provided projection data; and
determining the fractional flow reserve value by using a fractional flow reserve value determination algorithm that is configured to determine the fractional flow reserve value based on a boundary condition and the provided representation of the coronary artery system by a fractional flow reserve value determination unit.

13. A non-transitory computer program for determining a fractional flow reserve value of the coronary artery system of a living being, the computer program comprising program code means for causing an apparatus to carry out the steps of:
providing a representation of the coronary artery system by a representation providing unit;
generating radiation with a radiation source of a projection data providing unit during a contrast enhanced scan of an aorta of a living being;
irradiating a detector of the projection data providing unit with the radiation, wherein the detector has several rows of detection elements used for generating projection data and wherein not all rows of the detection elements are irradiated, but only one row is irradiated by a single fan beam or at least one row is irradiated by several fan beams;
providing projection data generated by the detector of the projection data providing unit based on the radiation,
determining a boundary condition which is specific for the living being by a boundary condition determination unit based on the provided projection data; and
determining the fractional flow reserve value by using a fractional flow reserve value determination algorithm that is configured to determine the fractional flow reserve value based on a boundary condition and the provided representation of the coronary artery system by a fractional flow reserve value determination unit.

14. The non-transitory computer program of claim 13, wherein the steps further include:
reconstructing an image showing the coronary artery system and surrounding regions, which surround vessels of the coronary artery system, over time based on the provided projection data and to determine an amount of blood leaving the coronary artery system based on the image as the boundary condition.

15. The non-transitory computer program of claim 14, wherein the steps further include:
    determining the amount of blood leaving the coronary artery system based on image values of image elements showing the surrounding regions.

16. The non-transitory computer program of claim 15, wherein the steps further comprise:
    determining a myocardial tissue value being indicative of an uptake of a part of a contrast agent in the myocardial tissue based on the image values of the image elements showing the surrounding regions and to determine the amount of blood leaving the coronary artery system based on the myocardial tissue value.

17. The non-transitory computer program of claim 15, wherein the steps further comprise:
    determining which image elements showing the surrounding regions represent side branches of the vessels of the coronary artery system, which are too small for being represented by the provided representation of the coronary artery system, based on the image values of the image elements showing the surrounding regions and to determine the amount of blood leaving the coronary artery system through the side branches based on the determined image elements.

18. The non-transitory computer program of claim 13, wherein the steps further comprise:
    determining a flow velocity and/or dimensions of the coronary arteries at the outlets of the coronary artery system as a boundary condition.

19. The non-transitory computer program of claim 13, wherein the steps further comprise:
    providing anatomical and/or physiological properties of the living being, and determining the boundary condition based on the provided properties of the living being.

20. The non-transitory computer program of claim 13, wherein the steps further comprise:
    providing a cross-section area of a vessel of the coronary artery system and/or a myocardial mass and/or a ratio of diameters of a vessel and its branch of the coronary artery system and/or the heart size and/or the ejection fraction of the heart and/or the stroke volume of the heart as the property.

* * * * *